United States Patent [19]

Ireland et al.

[11] Patent Number: 5,411,513

[45] Date of Patent: May 2, 1995

[54] TRANSMISSION MECHANISM FOR A SURGICAL CUTTING INSTRUMENT

[75] Inventors: Dan D. Ireland, Martinsville; Michael E. Miller, Indianapolis, both of Ind.

[73] Assignee: Danek Medical, Inc., Memphis, Tenn.

[21] Appl. No.: 201,277

[22] Filed: Feb. 24, 1994

[51] Int. Cl.⁶ .............................................. A61B 17/32
[52] U.S. Cl. ...................................... 606/171; 604/22
[58] Field of Search ............... 606/167, 168, 170, 171, 606/180, 177; 604/22

[56] References Cited

U.S. PATENT DOCUMENTS

| | | | |
|---|---|---|---|
| 4,210,146 | 7/1980 | Banko | 606/171 |
| 4,246,906 | 1/1981 | Martinez | 606/171 |
| 4,589,414 | 5/1986 | Yoshida et al. | 606/171 |
| 4,753,234 | 6/1988 | Martinez | 606/171 |
| 5,059,204 | 8/1991 | Lawson et al. | 606/171 |
| 5,201,749 | 4/1993 | Sachse et al. | 606/171 |

Primary Examiner—Stephen C. Pellegrino
Assistant Examiner—William W. Lewis
Attorney, Agent, or Firm—Woodard, Emhardt, Naughton, Moriarty & McNett

[57] ABSTRACT

A reciprocating cutting instrument includes an outer tube housing an inner reciprocating cutting blade. The cutting blade is engaged to a source of power, namely a motor, through a transmission and drive mechanism. This transmission and drive mechanism converts rotary drive movement of the motor to reciprocating movement of the cutting blade. A cam is provided that engages the spindle of the motor, the cam formed by a generally cylindrically shaped cam barrel with a cam channel defined in the outer surface of the barrel. A drive ball rides within the channel and is supported within a boss of a linear in-line driver. The in-line driver reciprocates within a bearing housed by a driver cartridge. Pressure between the drive ball and the cam channel is maintained by a set screw threaded into the boss in the in-line driver. As the motor rotates, the spindle, which is engaged to the cam, rotates the cam barrel. The rotation of the cam barrel causes the cam channel to pass underneath the drive ball, which forces the drive ball to follow the channel path. In one preferred embodiment, the channel path is in the form of a harmonic curve so that the drive ball will reciprocate through a particular stroke during a full rotation of the cam.

9 Claims, 4 Drawing Sheets

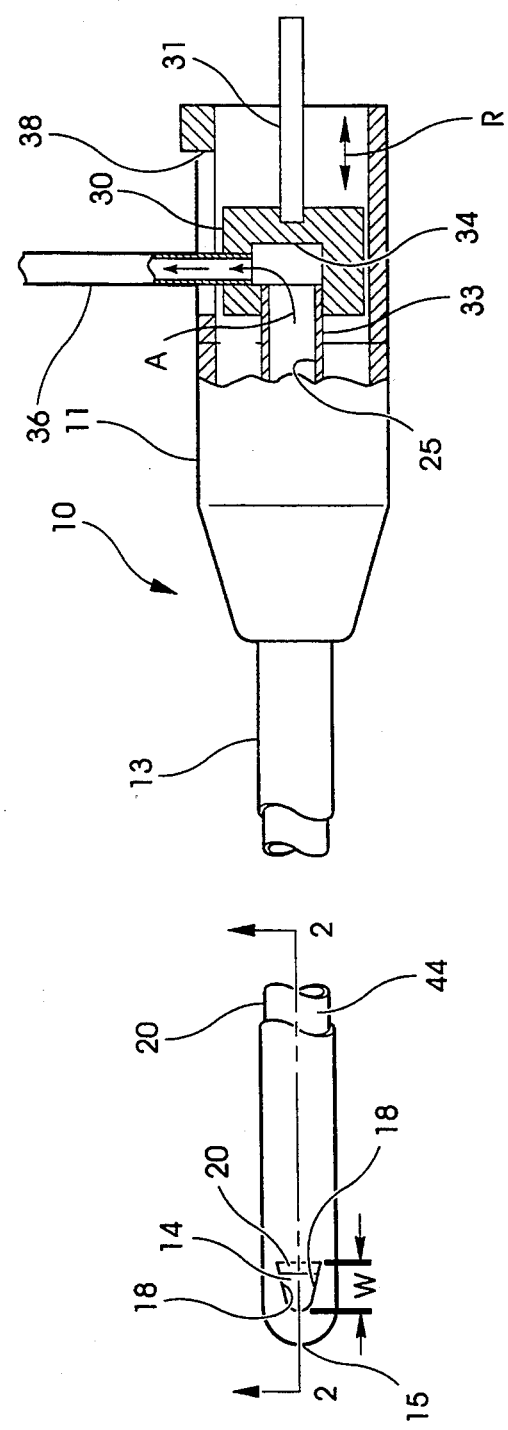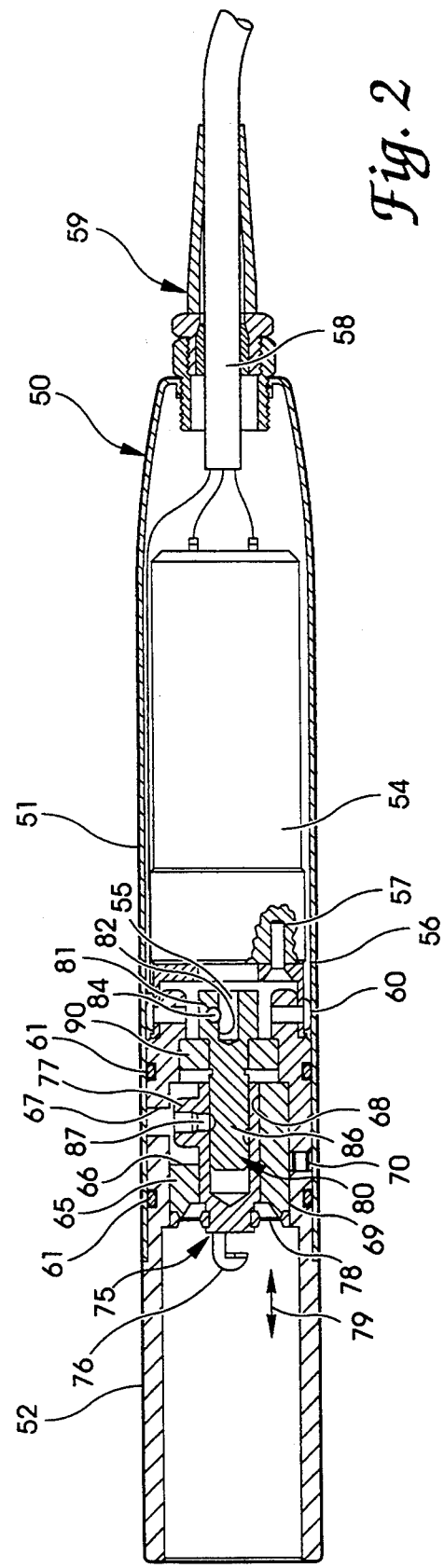

TRANSMISSION MECHANISM FOR A SURGICAL CUTTING INSTRUMENT

BACKGROUND OF THE INVENTION

The present invention relates to a percutaneous or intratrocar surgical instrument for the excision and removal of a wide range of tissues. More particularly, a surgical cutting instrument is disclosed which is particularly adapted for a wide range of operating speeds and which is capable of cutting tough tissue, such as may be found during orthopaedic or spinal surgery. The present invention has application in a wide range of procedures, although the following disclosures will pertain principally to minimally invasive cutting instruments used in the orthopaedic or spinal surgical fields. The present disclosure specifically addresses a transmission mechanism for converting, in one embodiment, rotary output from a motor to linear reciprocation of the cutting blade.

One problem that is frequently diagnosed and treated in the field of spinal surgery concerns degeneration or herniation of the intervertebral disk. In the past, treatment of these diagnosed conditions has required complicated and highly invasive surgical procedures, often involving some degree of fusion between adjacent vertebrae serviced by the affected intervertebral disk. In these procedures it is important that the affected disk be entirely removed for replacement by bone graft material. In some cases, a prosthetic disk may be implanted.

Within the last decade, techniques for percutaneous diskectomies have been developed. One such system is described in the patent to Onik, U.S. Re. Pat. No. 33,258. The Onik device, like other known devices, is a "tube within a tube" cutting instrument which incorporates a reciprocating inner cutting sleeve operating within the central bore of an outer cutting sleeve. Typically, the excised disk material is suspended in a saline irrigation fluid which is aspirated through the central passageway of the inner cutting sleeve.

Similar cutting devices are represented in U.S. Pat. Nos. 4,246,902 to Martinez, and 5,106,364 to Hayafuji. While these aforementioned devices utilize linearly reciprocating cutters, another genre of surgical instruments implement a rotary cutting action. Such a device is represented by the patent to Bonnell et al., U.S. Pat. No. 4,203,444.

The tissue cutting instruments presently available in the art suffer from a variety of problems. For example, rotary cutters have a tendency to become clogged as the excised tissue "spools" or winds around the shaft driving the rotating cutter blade. This spooling can clog the aspiration channel of the cutter and even stall the blade or motor.

Another problem common between rotary and linearly reciprocating devices is their general inability to cut very tough tissue, at least using an instrument that is adapted for percutaneous insertion. Certainly larger cutting instruments driven by larger motors are capable of cutting very tough or hard tissue. However, no prior device has been able to avoid the trade-off between a minimally invasive cutting instrument and the ability to cut these types of tough tissue.

With respect to reciprocating or linear cutters, the drive motors for such devices tend to be larger than rotary motors. It can certainly by appreciated that one consideration in the design of a percutaneous surgical cutting instrument is the size of the device. The surgeon must be able to deftly manipulate the cutting instrument while performing a procedure such as a discectomy. It is therefore an important design criterion that the cutting instrument fill as small an envelope as possible, a criterion that is more easily fulfilled by the use of a rotary motor.

There is a need in the field of tissue excision and removal for a surgical cutter that is adapted for minimally invasive uses, but that is still capable of cutting hard or tough tissue encountered in spinal and orthopaedic procedures, for example. The cutting instrument must be capable of excising the tissue cleanly, without tearing, and of aspirating the tissue pieces efficiently and without clogging. The instrument must also be efficiently packaged and smaller than a typical reciprocating cutting instrument. These and other needs in the industry are addressed by the present invention.

SUMMARY OF THE INVENTION

In order to address the needs of surgical cutting instruments, a transmission and drive mechanism has been provided which can convert rotary drive movement to reciprocating movement of the cutting blade. The use of a rotary motor can permit higher torques in a smaller package than may be achieved by a reciprocating motor of comparable output power and input energy requirements. Consequently, in accordance with the invention, a cam is provided that engages the spindle of the motor. In the preferred embodiment, the cam is generally cylindrical in shape with a cam channel defined in the outer surface of the cam barrel. A drive ball rides within the channel and is supported within a boss of a linear in-line driver. The in-line driver reciprocates within a bearing supported by a driver cartridge. Pressure between the drive ball and the cam channel is maintained by a set screw threaded into the boss in the in-line driver.

As the motor rotates, the spindle, which is engaged to the cam, rotates the cam. The rotation of the cam and cam barrel causes the cam channel to pass underneath the drive ball, which forces the drive ball to follow the channel path. In one preferred embodiment, the channel path is in the form of a harmonic curve so that the drive ball will reciprocate through a particular stroke during a full rotation of the cam. In other alternative embodiments, the cam channel can assume a variety of paths around the circumference of the cam barrel. One such path would multiply the number of reciprocations for one revolution of the cam barrel.

DESCRIPTION OF THE FIGURES

FIG. 1 is a partial cutaway view of the portion of a surgical cutting instrument housing the cutting blade driven by the transmission and drive mechanism of the present invention.

FIG. 2 is a side cross-sectional view of the transmission and drive mechanism for use in connection with the cutting instrument depicted in FIG. 1.

DESCRIPTION OF THE PREFERRED EMBODIMENTS

Figure 3:
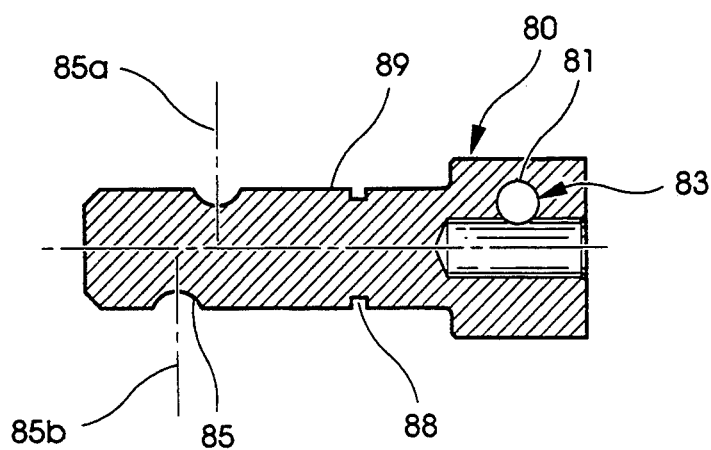
FIG. 3 is an enlarged cross-sectional view of the cam incorporated into the transmission and drive mechanism shown in FIG. 2.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

A portion of a surgical cutting instrument 10 is shown in FIG. 1 which is adapted for percutaneous insertion at the surgical site and is specifically adapted to cut tissue in the spinal region. However, the same instrument could be used in other orthopaedic, such as an arthroscopic surgery of the knee, or similar surgical procedures, such as removal of the gall bladder or prostate. FIG. 1 depicts only the cutting portion of the instrument, this portion being engaged to a transmission and drive portion described herein.

The instrument 10 includes a hand piece 11 which supports an outer cannula 13. The outer cannula has a blunt distal tip 15 to minimize trauma to tissue as the cutting instrument is manipulated in the surgical site. The outer cannula 13 includes a cutting opening 14 formed therethrough which opens to a central bore 16 extending through the length of the cannula 13. The cutting opening 14 defines a cutting edge 18, which in one embodiment is defined by a beveled cut in the wall of the outer cannula. In the illustrated embodiment, the cutting opening 14 is in the shape of an isosceles triangle. The cutting edge 18 in the specific embodiment is defined at the side of the triangle, but excludes the base of the triangular shape as shown in FIG. 1.

The cutting instrument 10 further includes an inner cannula 20 which is slideably and concentrically disposed within the outer cannula 13. The inner cannula 20 terminates in a cutting edge 22 at the end opening 23 of the cannula. The end opening 23 opens into an aspiration passageway 25 extending through the entire length of the inner cannula 20.

The outer cannula 13 is supported by the hand piece 11, while the inner cannula 20 also extends into the hand piece 11 to engage a drive mount 30 at a cannula support portion 33. The drive mount is engaged to a drive rod 31 that is connected to a motor or suitable mechanism for providing reciprocating motion. Specifically, the drive rod 31 and mount 30 reciprocates axially in the direction of the arrows R shown in FIG. 1. Since the inner cannula 20 is fixed to the drive mount 30 it too reciprocates within the outer cannula 13. As the inner cannula 20 reciprocates, the inner surface of the outer cannula and the outer surface of the inner cannula operate as a bearing surface for the smooth movement of the inner cannula.

The drive mount 30 can include an aspiration chamber 34 which is connected through an aspiration tube 36 to a suitable vacuum source and tissue collection chamber in a manner well known in the art. In this particular embodiment, the aspiration tube 36 is engaged to the reciprocating drive mount 30. This aspect requires the definition of a slot 38 in the hand piece 11 to allow the tube 36 room to move as it reciprocates with the drive mount.

As thus far described, the instrument 10 incorporates many features of known reciprocating cutters, particularly those implementing the "tube within a tube" approach. It is understood that other reciprocating cutter portions are contemplated, the foregoing being provided for illustrative purposes. The present invention contemplates a transmission and drive portion for providing reciprocating motion to the drive rod 31. It is understood that the disclosed transmission and drive portion could be adapted to impart reciprocating movement to the cutter 20 using a number of interfaces that may or may not include a drive rod 31.

One embodiment of this transmission and drive portion is depicted in FIG. 2. In particular, a transmission and drive portion 50 is shown which can be suitably engaged to the cutting portion of the surgical cutting instrument 10 shown in FIG. 1. The transmission and drive portion 50 includes a driver cover 51 which houses the transmission and drive mechanism of the assembly. A driver cartridge 52 is affixed to the open end of the driver cover 51. A pair of sealing O-rings 61 are disposed between the driver cartridge 52 and the driver cover 51. These sealing O-rings provide, in one aspect, a means for removably engaging the cartridge 52 to the cover 51 in a press fit relationship. This relationship facilitates assembly of the device and disassembly to service the movable components of the transmission and drive mechanism housed therein.

The driver cover 51 supports a motor 54, which in the preferred illustrated embodiment is a rotary motor. Specifically, the motor 54 provides a rotational driving force through its drive spindle 55. The motor 54 is supported within the driver cover 51 by way of a motor cap 56, which is attached to the motor by a number of screws 57. A power cable 58 supplies electrical current to the monitor. The power cable 58 is supported on the driver cover 51 by a strain relief collet assembly 59 engaged at one end of the cover.

The driver cartridge 52 is attached to the motor cap 56 by a pair of cartridge mounting screws 60. As indicated previously, the driver cover 51 is supported by the cartridge 52 through the seal ring 61. This particular configuration, that is the arrangement of driver cover 51, cartridge 52 and the motor 54 and its power components, facilitates assembly of the complete transmission and drive portion. In particular, the motor drive spindle 55 can be first engaged to the motor 54 by way of the screws 57. The cap 56 is then attached to the driver cartridge 52 by way of the screws 60. The power cable 58 can be threaded through the collet assembly 59 and the driver cover 51 and attached to the motor, with the driver cover situated downstream on the power cable. Once the cable is connected to the electrical leads of the motor, the collet assembly 59 and driver cover 51 can be slid along the power cable until the driver cover achieves its press fit engagement with the sealing O-rings 61 and the driver cartridge 52. The collet assembly 59 can then be tightened to clamp the power cable to the driver cover 51. Disassembly can be readily achieved by reversing the above described steps.

The driver cartridge 52 supports a linear in-line bearing 65. In one embodiment, the bearing can be adhered to the inner bore of the driver cartridge 52. Alternatively, the bearing can be press fit into position, or a set screw 70 can be used to clamp the in-line bearing 65 to the driver cartridge 52, as depicted in FIG. 2. This linear in-line bearing 65 is generally cylindrical in shape, with a recess portion 66 formed in one side for purposes described herein. An access bore 67 is formed in the driver cartridge 52 which aligns with the boss recess 66 of the in-line bearing 65. The in-line bearing defines a central bore 68 and an outer surface 69 which contacts the driver cartridge 52.

Reciprocatably disposed within the in-line bearing 65 is an in-line driver 75. This driver includes at its free end an engagement clip 76 which can be suitably configured to engage a mating portion attached to the drive rod 31 of the cutter portion of the instrument 10, as shown in FIG. 1. Many such engagement mechanisms can be utilized that can accomplish a quick attachment and disconnect capability. One such example is illustrated in U.S. Pat. No. 4,911,161 to Schecter. This patent illustrates two such connection mechanisms in FIGS. 4 and 5 and their accompanying text. A person of ordinary skill in the art would be able to accomplish many such similar fixations between the driver components shown in FIG. 2 and the driven cutting components shown in FIG. 1.

The in-line driver 75 includes a boss 77 projecting outwardly therefrom. This boss 77 is adapted to reciprocate within the boss recess 66 in the in-line bearing 65. At its free end, the in-line driver 75 is connected to the driver cartridge 52 by way of a flex ring seal 78. As the in-line driver 75 reciprocates in the direction of the arrows 79, the flex ring seal 78 expands and contracts accordingly, while continuously maintaining a tight seal between the cutting portion of the instrument and the transmission and drive portion 50 of the instrument. It should be appreciated that since the cutting instrument portion shown in FIG. 1 utilizes vacuum and fluid flow, it is important to maintain a tight seal between these two portions of the cutting instrument 10.

The reciprocating motion is imparted to the in-line driver 75 by way of a first and second cam elements which form a transmission means, or a means for converting the rotary movement of the drive spindle 55 of the motor 54 to a reciprocating movement of the in-line driver 75. In the preferred embodiment, the first cam element is a cam 80. The cam 80 is engaged to the motor drive spindle 55 at a cam head 81.

Figure 4:
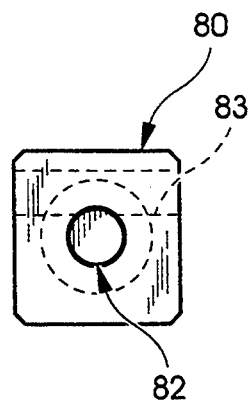
FIG. 4 is an end elevational view of the cam shown in FIG. 3.

Details of the cam 80 can be seen in FIGS. 3 and 4. The cam head 81 includes a spindle bore 82 which is sized to closely receive the drive spindle 55 therein. Transverse to the spindle bore 82 is a dowel bore 83 which intersects or overlaps a portion of the spindle bore 82. A tapered dowel 84 is inserted into the dowel bore 83 to bear against the drive spindle 55 when it is disposed within the spindle bore 82. The dowel is preferably slightly shorter than the length of the dowel bore 83. It is understood that the taper of the dowel facilitates its insertion into the bore and particularly its passage across the drive spindle 55 to form the press fit clamping engagement.

In an important feature of the invention, the cam 80 includes a cam channel 85 carved into the outer surface of the cam barrel 89. This cam channel is preferably cut into the barrel 89 in the form of a circular segment less than a semi-circle so that the channel receives only a lower portion of a cam follower, which in the preferred embodiment is a drive ball 86. As shown in FIG. 2, this drive ball is substantially housed within the boss 77 of the in-line driver 75, which constitutes the second cam element of the transmission means. The set screw 87 presses against the drive ball to maintain its contact within the cam channel 85. It is understood that other cam channel and cam follower configurations may be contemplated. However, it is believed that the ball and channel configuration is optimal to reduce friction and wear between the components.

The cam 80 is rotatably supported not only by the drive spindle 55 of the motor 54, but also by a shielded ball bearing 90, which bearing is supported between the driver cartridge 52 and the cam barrel 89. A snap ring groove 88 can be provided in the cam barrel 89 to further lock the cam into position within the driver cartridge 52.

Figure 5:
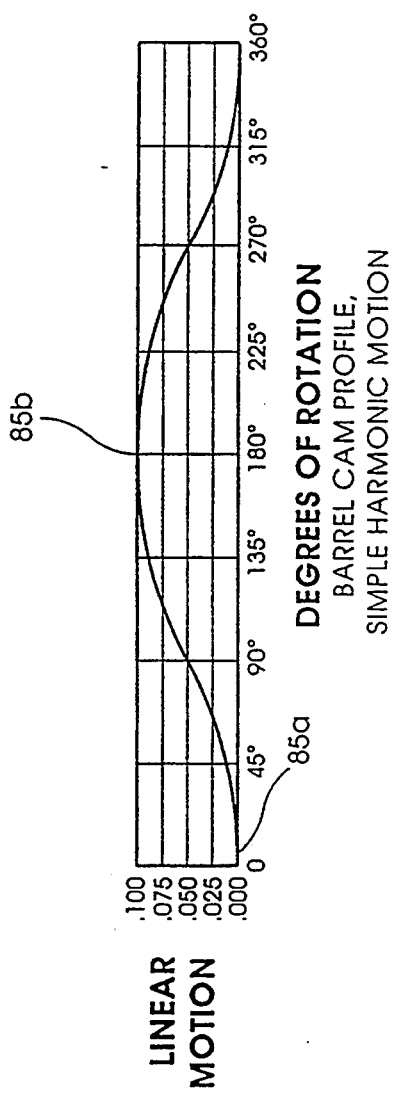
FIG. 5 is a graph illustrating the cam relationship between rotation of the drive motor and linear stroke of the cutting blade.

In operation, the rotary motion imparted by the motor 54 to the drive spindle 55 is directly translated to the cam 80 by its press fit engagement. As the cam rotates, the cam channel 85 transverses directly beneath the drive ball 86. As shown in FIG. 5, the cam channel is more than simply a circumferential channel cutting through a plane perpendicular to the axis of the cam 80. More particularly, the channel has a harmonic shape so that portions of the channel at 180° opposite locations are displaced from each other axially along the length of the barrel. Specifically, as shown in FIGS. 3 and 5, the portion of the channel at location or apex 85a is axially offset by 0.254 cm. from location or apex 85b that is offset by 180° around the cam barrel. Consequently, as the cam 80 rotates and the ball is forced to move within the channel, it too will translate linearly in accordance with the harmonic curve shown in FIG. 5. As the ball translates, and because it is trapped within the boss 77, the in-line driver 75 will consequently reciprocate in the manner shown in FIG. 5.

It is understood that the cam channel 85 can have various configurations. It has, however, been found for the preferred embodiment that a simple harmonic curve provides the smoothest and most efficient translation of the rotary motion of the motor 54 to the reciprocating motion of the cutting blade shown in FIG. 1. It should also be appreciated that greater linear strokes can be achieved by offsetting the 180° opposite apexes of the cam channel by a greater dimension than that shown in FIG. 5. This would, of course slightly skew the motion curve and modify the acceleration of the cutting blade at various points in the rotation of the cam 80.

Figure 6:
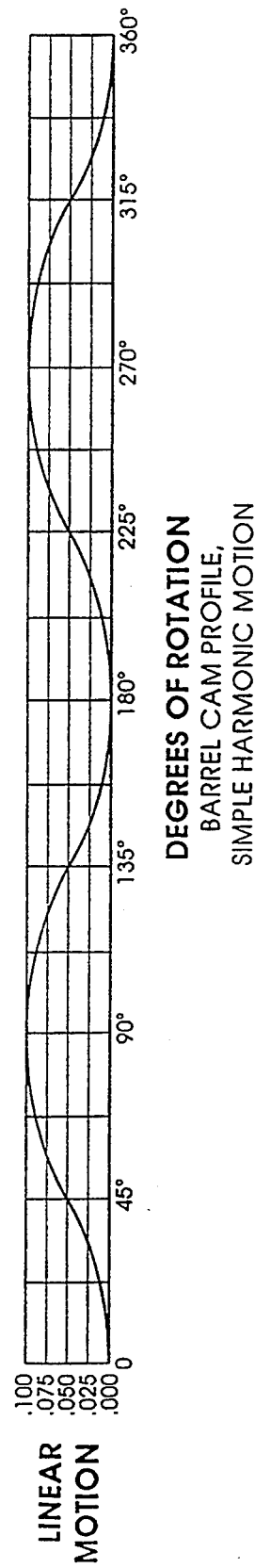
FIG. 6 is a graph illustrating an alternative cam relationship between motor rotation and linear stroke of the cutting blade in which the blade reciprocates through two cycles for a single revolution of the motor and cam.

It should also be understood that in the preferred embodiment, a single revolution of the cam produces a single forward and return stroke of the cutting blade. Multiplication of the reciprocating speed can be achieved by providing more than two apexes to the cam channel 85, as depicted in the graph of FIG. 6. It can therefore be seen that several cams could be provided that would be readily removed and replaced within the transmission and drive portion 50 of the cutting instrument 10. When greater cutting speeds are required, a cam having a cam channel with several apexes could be provided. It can be expected, however, that the actual cutting force that would be imparted at the higher cutting speeds would be decreased even as the speeds are increased. Conversely, a reduction in the reciprocating speed would increase the actual cutting power achieved by the blade, which may be necessary when operating on tougher tissues.

Figure 7:
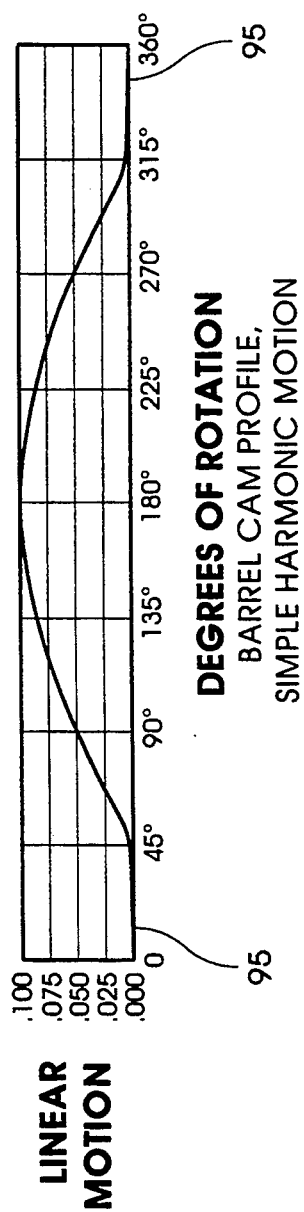
FIG. 7 is a graph illustrating an alternative cam relationship between motor rotation and linear stroke of the cutting blade in which the blade dwells at a predetermined point in its cycle.

In a further alternative embodiment, the cam channel can be configured as depicted in the graph of FIG. 7. In this configuration, the cam channel includes a dwell region 95 in the ranges 0°–45° and 315°–360°. In essence, in this dwell region 95 the cam channel will not include any axial offset component so that the cam follower will not stroke in the linear direction. These dwell regions will result in a dwell in the movement of the cutter blade, which in the embodiment depicted in FIG. 7 occurs at the beginning of the stroke. This dwell region 95 can be provided, for example, to allow greater amounts of tissue to be drawn into the cutting opening 14 of the instrument before the cutter is advanced to slice the tissue. The dwell region could be arranged at any portion of the cutter stroke depending upon the perceived needs of the cutting instrument.

In the specific illustrated embodiment, the cam itself is approximately 28.5 cm long. The offset of the 180° apexes 85a and 85b of the cam channel are approximately 2.54 cm. The cam 80 is preferably formed of 420 stainless steel, as is the drive ball 86. It is believed that the stainless steel mating surfaces provide a better wear resistant rolling surface to translate the rotary motion to reciprocating motion. Naturally, certain biocompatible lubricants could be applied between the drive ball and the cam channel. The inline bearing 65 can be formed of a plastic such as delrin or other material that exhibits suitable wear characteristics when supporting a component such as the inline driver 75. The driver 75 may also be formed of a plastic or stainless steel.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. For example, the first cam element, or the cam 80, can be engaged to the engagement clip 76, and the inline driver 75 can be configured to engaged the motor drive spindle 55. In this orientation, rotary motion is transmitted through rotation of the driver 75, through the ball 80 and to the channel 85 of the cam barrel 89. Since the driver 75 in this configuration is essentially fixed to linear movement, the cam 80 must necessarily reciprocate as it is acted upon by the ball 80.

What is claimed is:

1. A tissue cutting apparatus, comprising:
   a motor driving a rotating output shaft;
   an outer housing configured for insertion into a body site;
   a cutting blade for cutting body tissue at the body site, the cutting blade configured for reciprocating movement within said outer housing;
   transmission means disposed between said motor and said cutting blade for converting rotary motion from said output shaft to reciprocating linear motion of said cutting blade, said transmission means including;
   a first cam element connected to one of said output shaft and said cutting blade, said first cam element having a cylindrical surface with a channel defined continuously around the circumference thereof;
   a second cam element connected to the other of said output shaft and said cutting blade; and
   a cam follower element disposed between said first cam element and said second cam element with a portion of said cam follower element slidably disposed within said channel,
   whereby said cam follower element traverses along said channel continuously about said cylindrical surface as one or the other of said first cam element of said second cam element rotates with said output shaft.

2. The tissue cutting apparatus of claim 1, wherein:
   said first cam element includes a cam barrel removably connected at a first end to said output shaft, with said cylindrical surface at an opposite end thereof; and
   said second cam element is connected to said cutting blade.

3. The tissue cutting apparatus of claim 1, wherein said continuous channel defines a curve around the circumference of said cylindrical surface in which portions of said curve are offset along an axial length of said cylindrical surface from each other.

4. The tissue cutting apparatus of claim 3, wherein said continuous channel includes a dwell region in which successive positions along said channel are not axially offset relative to each other, thereby producing a dwell in the linear motion of said cutting blade when said cam follower traverse said dwell region.

5. The tissue cutting apparatus of claim 3, wherein said continuous channel in said cylindrical surface defines a harmonic curve.

6. The tissue cutting apparatus of claim 5, wherein said continuous channel defines two harmonic curves connected to each other.

7. The tissue cutting apparatus of claim 3, wherein said curve defines two apexes at 180° opposite locations around the circumference of said cylindrical surface such that one revolution of said output shaft produces one cycle of reciprocating linear motion of said cutting blade.

8. The tissue cutting apparatus of claim 3, wherein said curve defines more than two apexes, such that one revolution of said output shaft produces more than one cycle of reciprocating linear motion of said cutting blade.

9. The tissue cutting apparatus of claim 1, wherein:
   said cam follower is a ball configured to be partially received within said channel; and
   said second cam element includes means for supporting said ball such that said second cam element moves with said ball as said ball traverses said channel.

* * * * *

UNITED STATES PATENT AND TRADEMARK OFFICE
CERTIFICATE OF CORRECTION

PATENT NO. : 5,411,513

DATED : May 2, 1995

INVENTOR(S) : Dan D. Ireland, et al.

It is certified that error appears in the above-indentified patent and that said Letters Patent is hereby corrected as shown below:

On the title page, item [75], change "Dan D. Ireland" to --Dan C. Ireland--.

Column 4, line 46, change "monitor" to "motor".

Column 6, line 24, change "transverses" to "traverses".

Signed and Sealed this

Nineteenth Day of March, 1996

Attest:

BRUCE LEHMAN

*Attesting Officer*                *Commissioner of Patents and Trademarks*